US00PP37778P3

(12) United States Plant Patent
Skotak, Jr.

(10) Patent No.: US PP37,778 P3
(45) Date of Patent: Oct. 13, 2026

(54) ***AECHMEA* PLANT NAMED 'A2191'**

(50) Latin Name: *Aechmea chantinii*
Varietal Denomination: A2191

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 0 days.

(21) Appl. No.: 19/401,690

(22) Filed: Nov. 26, 2025

(65) Prior Publication Data

US 2026/0157248 P1 Jun. 4, 2026

(30) Foreign Application Priority Data

Nov. 29, 2024 (QZ) ..... PBR 2024/2861

(51) Int. Cl.
*A01H 5/02* (2018.01)
*A01H 5/12* (2018.01)
*A01H 6/22* (2018.01)

(52) U.S. Cl.
USPC ..... Plt./370
CPC ..... *A01H 6/22* (2018.05); *A01H 5/02* (2013.01); *A01H 5/12* (2013.01)

(58) Field of Classification Search
USPC ..... Plt./370
CPC ... A01H 5/02; A01H 5/00; A01H 6/22; A01H 6/223
See application file for complete search history.

(56) References Cited

PUBLICATIONS

CPVO Application Consultation Version 4.25.12 retrieved on Mar. 18, 2026 at https://online.plantvarieties.eu/publicConsultationDetails?registerId=20242861&denomination=a2191, 2 pp. (Year: 2026).*
Luther, New Taxa of Bromeliaceae (V), Selbyana 10: 56-59, 1987. (Year: 1987).*

* cited by examiner

*Primary Examiner* — June Hwu
(74) *Attorney, Agent, or Firm* — James R. Holm; Plant Novelty Rights, LLC

(57) ABSTRACT

A new and distinct *Aechmea* plant named 'A2191' particularly distinguished by a highly intense, deep red inflorescence coloration; a compact growth habit with small and dense rosettes; a unique leaf pattern characterized by strong and regular silver banding on dark green foliage; a uniform and vigorous plantlet development under tissue culture; and a high ornamental value due to its contrasting leaf colorations and proportional plant form.

3 Drawing Sheets

Genus and species: *Aechmea chantinii.*
Variety denomination: 'A2191'.

STATEMENT REGARDING PRIOR DISCLOSURES BY THE INVENTOR

This application claims priority to CPVO application no. 2024/2861 filed on Nov. 29, 2024, which is herein incorporated by reference. The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the effective filing date.

BACKGROUND OF THE NEW PLANT

The present invention comprises a new and distinct variety of *Aechmea* plant, botanically known as *Aechmea chantinii*, and hereinafter referred to by the variety name 'A2191'.

*Aechmea* comprises a genus of more than 168 species of evergreen perennials suitable for cultivation in the home or in the greenhouse. *Aechmea* may be terrestrial or epiphytic.

For the most part, the species vary in diameter from 12 to 18 inches to 3 or 4 feet and have rosettes of spiny-edged leaves.

Flowers and bracts of *Aechmea* frequently have brilliant colors and may last for several months. The range of colors for *Aechmea* is generally from the yellow through orange but may also include pink, orange, red and red-purple. Tubular, three-petalled flowers may also appear but are usually short-lived.

*Aechmea* may be grown as pot plants for greenhouse or home use. Typically, the plants are shaded from direct sunlight; and the central, vaselike part of the leaf rosette is normally filled with water.

*Aechmea* is native to tropical America. Leaves of *Aechmea* are usually formed from basal rosettes which are entire and in several vertical ranks. *Aechmea* has terminal spikes or panicles which are often bracted with petals united in a tube longer than the calyx.

Asexual propagation of *Aechmea* is frequently done through meristematic tissue culture. Propagation can also be from offshoots which can be detached from the mother plant and grown in an appropriate soil or bark mixture. Methods for cultivating and crossing of *Aechmea* are well known.

The new *Aechmea* variety 'A2191' is the product of a controlled cross pollination conducted by the inventor in Alajuela, Costa Rica in May 2014. The objective of the breeding program was to develop compact and uniform *Aechmea chantinii* plants with unique silver variegation on the leaves, deep red inflorescence, and plants suitable for pot production. The female or seed parent was an unnamed and unpatented *Aechmea chantinii* breeding line. The male or pollen parent was an unnamed and unpatented *Aechmea chantinii* breeding line. 'A2191' was selected by the inventor in June 2018 in Alajuela, Costa Rica as a single flowering plant from within the progeny of the stated cross.

The new *Aechmea* cultivar 'A2191' was first reproduced asexually by meristematic tissue culture in March 2020 at a commercial laboratory in Evergem, Belgium. Asexual propagation by meristematic tissue culture of the new variety has shown that the unique features of the new variety are stable and reproduced true-to-type to date through 5 successive generations.

SUMMARY OF THE INVENTION

The new *Aechmea* cultivar 'A2191' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Aechmea* cultivar. The combination of these characteristics distinguishes 'A2191' as a new and distinct variety of *Aechmea*.

1. *Aechmea* 'A2191' exhibits highly intense, deep red inflorescence coloration.
2. *Aechmea* 'A2191' exhibits a compact growth habit with small and dense rosettes.
3. *Aechmea* 'A2191' exhibits a unique leaf pattern characterized by strong and regular silver banding on dark green foliage.
4. *Aechmea* 'A2191' exhibits a uniform and vigorous plantlet development under tissue culture.
5. *Aechmea* 'A2191' exhibits high ornamental value due to its contrasting leaf colorations and proportional plant form.

DESCRIPTION OF THE PHOTOGRAPHS

This new *Aechmea* cultivar is illustrated by the accompanying-colored photographs which show the overall appearance and distinct characteristics of the plant. The colors shown are as true as can be reasonably obtained by conventional photographic procedures. The photographs are of 12-month-old plants grown in 12-centimeter circular containers in a conventional glass greenhouse in Evergem, Belgium. Colors in the photographs may differ slightly from the color values cited in the botanical description which accurately describes the colors of the new variety.

DESCRIPTION OF THE NEW VARIETY

Figure 1:
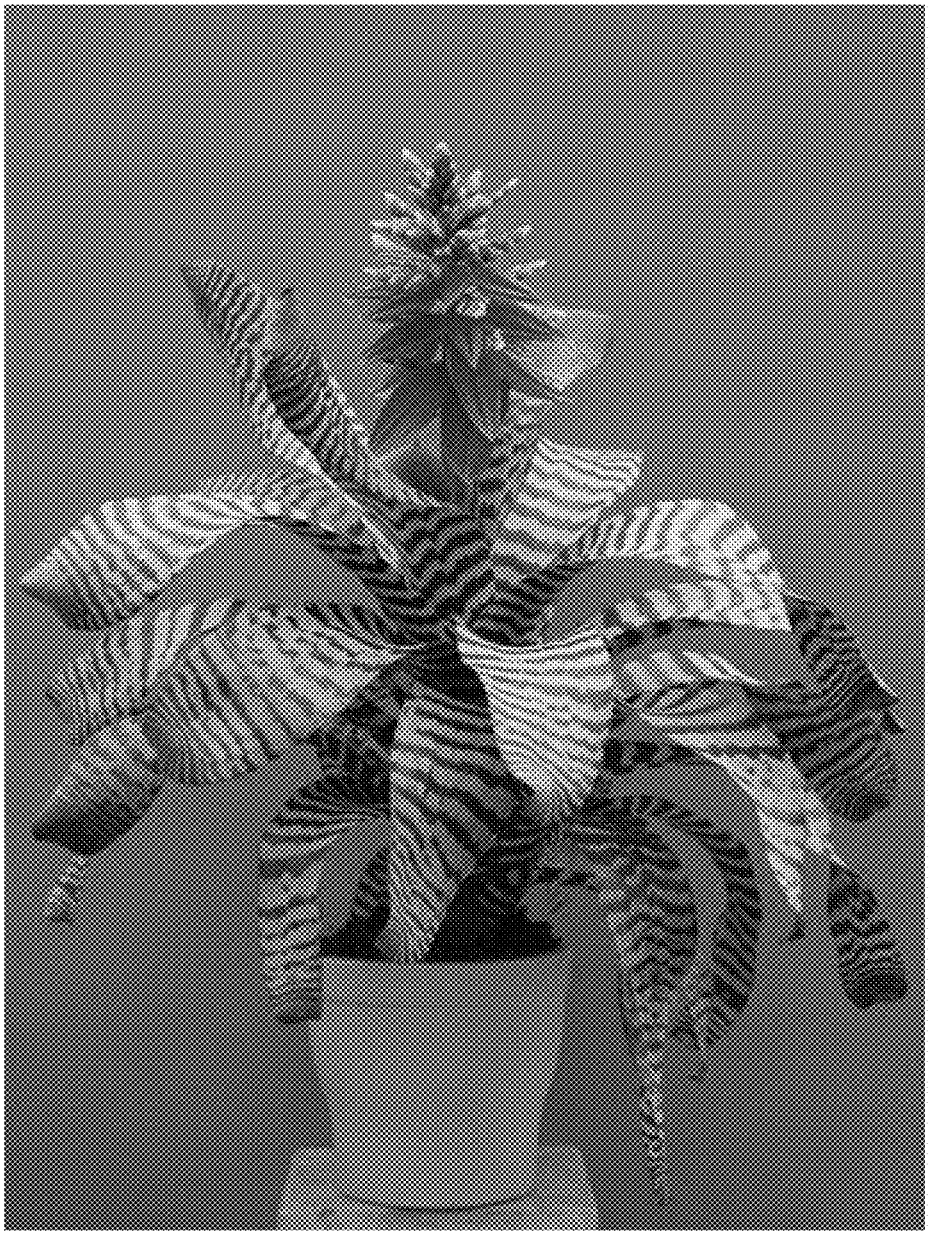
FIG. 1 shows the overall plant form, foliage, and inflorescence of 'A2191'.
Figure 2:
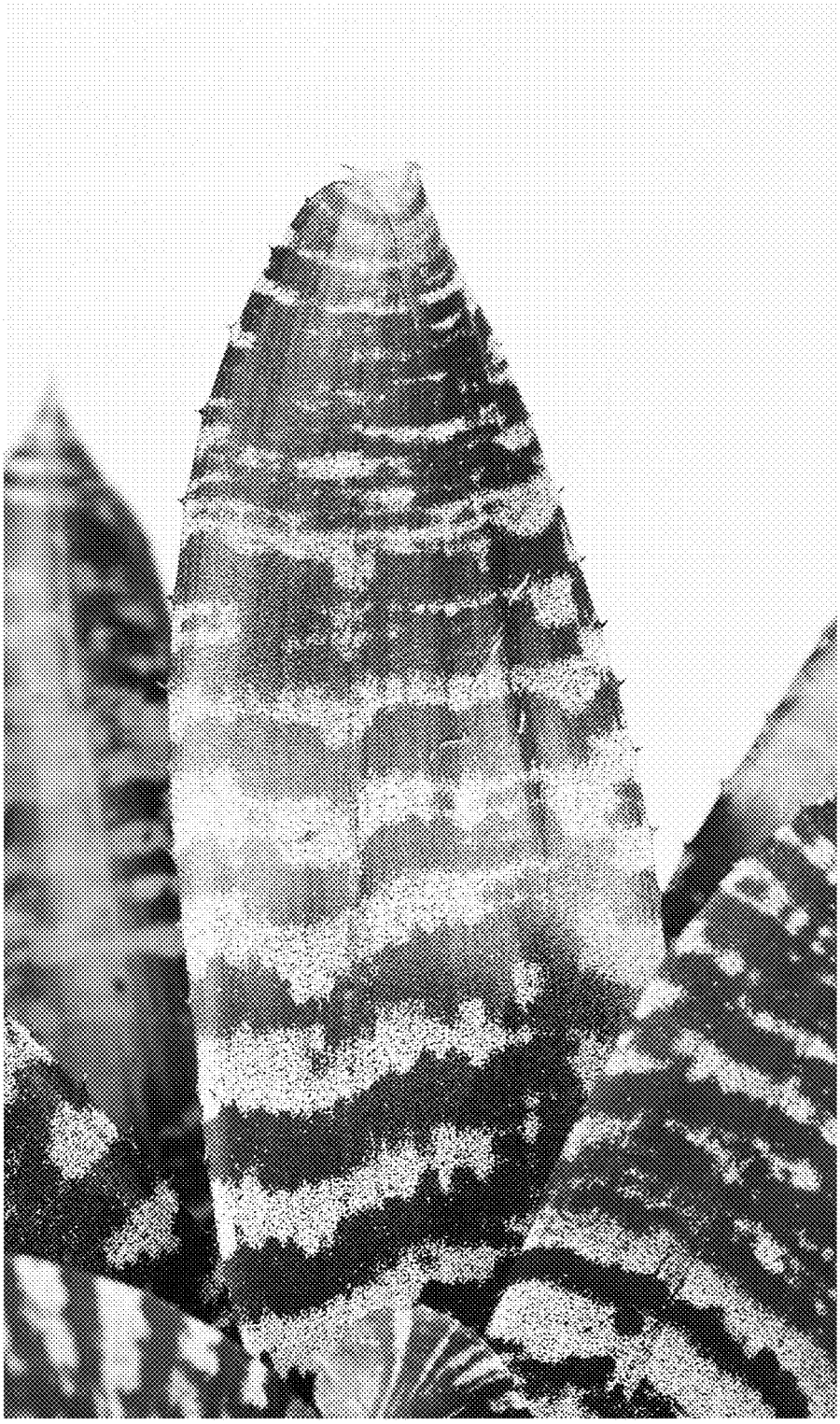
FIG. 2 shows a close-up of a typical leaf of 'A2191'.
Figure 3:
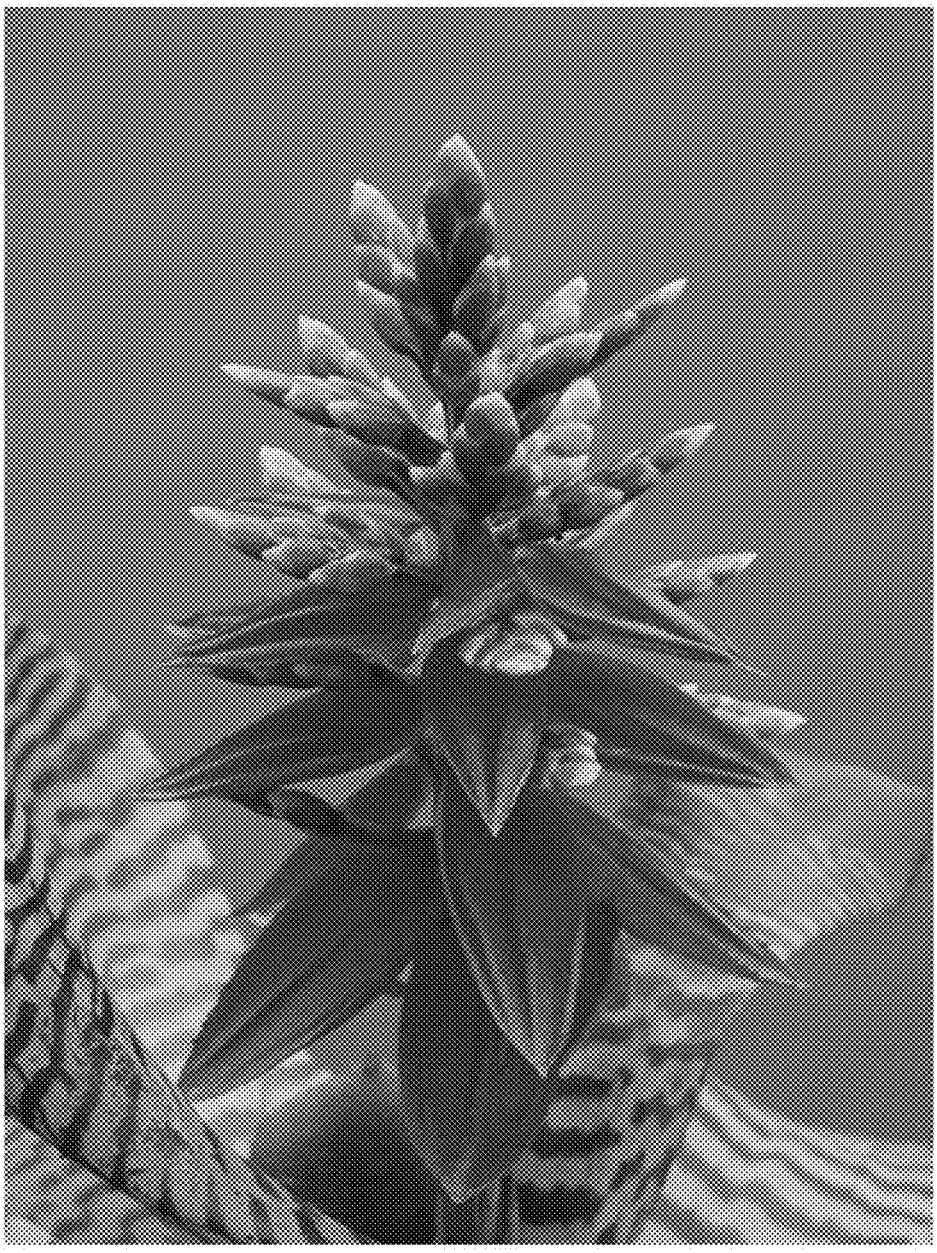
FIG. 3 shows a close-up of typical inflorescence of 'A2191'.

In the following description, color references are made to The Royal Horticultural Society Colour Chart, Sixth Edition, except where general color terms of ordinary dictionary significance are used.

The following observations and measurements describe 12-month-old plants grown in 12-centimeter circular containers in a conventional glass greenhouse located in Evergem, Belgium under normal light levels with no supplemental lighting. Average daily temperatures ranged between 21° C. and 23° C. and average nightly temperatures ranged between 19° C. and 21° C. Measurements and numerical values represent averages of typical plant types.

DETAILED BOTANICAL DESCRIPTION

Classification:

*Family*.—Bromeliaceae.

*Botanical*.—*Aechmea chantinii*.

*Denomination*.—'A2191'.

General description:

*Plant type*.—Tropical perennial suitable as an indoor potted plant.

*Growth habit*.—Highly symmetrical, compact and dense basal rosette; inflorescence grows from the center of the basal rosette.

*Overall plant shape*.—Obovate with a flattened top, inflorescence carried slightly above the foliar plane.

*Height from soil level to top of foliar plane*.—27.2 cm.

*Plant diameter or area of spread*.—27.7 cm.

*Growth rate*.—Moderate.

*Plant vigor*.—Moderate.

*Branching habit*.—No lateral branching; leaves in a basal rosette, inflorescence grows from the center of the basal rosette.

*Propagation type*.—Meristematic tissue culture.

*Time to produce a finished plant*.—Approximately 52 weeks from a tissue cultured plantlet.

Root description:

*General*.—Slightly fleshy and very slightly fibrous.

*Length*.—Average 6.8 cm.

*Width*.—Average 0.1 cm.

*Color*.—166C and 166D (greyed-orange).

Foliage description:

*Arrangement*.—Rosulate.

*Compound or single*.—Single.

*Quantity of leaves per rosette*.—23.

*Lamina*.—Shape: Oblong. Length: Average 22.6 cm. Width: Average 4.9 cm. Aspect: Flat to slightly concave towards the base, slightly twisted axially with older leaves curled slightly downwards. Apex shape: Broad and abruptly acute with a mucronulate tip. Base: Sheathing. Sheath length: Average 5.0 cm. Sheath width Average 5.9 cm. Sheath color: N148C (yellow-green) and edged 144A (yellow-green). Margin: Dentate with sharp teeth. Undulation: Coarsely undulate and slightly twisted axially. Lobes: Unlobed. Texture (both upper and lower surfaces): Smooth and glabrous. Rugosity: Non-rugose. Pubescence: No pubescence present. Luster: Upper surface: Glossy. Lower surface: Slightly glossy. Color: Juvenile foliage: Upper surface: A blend of NN137A and 147A (green to yellow-green) and blotched N155A and 198C (white to green-white) in radial lines across the lamina. Lower surface: A blend of 137B and 146A (green to yellow-green) and heavily blotched N155A and 198D (white to green-white) in radial lines across the lamina. Mature foliage: Upper surface: Slightly darker than a blend of NN137A and 147A (green to yellow-green), closest to 147A, and blotched N155A (white) in loosely arranged radial lines across the lamina.

Lower surface: NN137B (green) and heavily blotched N155A (white) in loosely arranged radial lines across the lamina. Venation: Pattern: Parallel. Color (mature foliage): Upper surface: Upper surface venation is colored the same as the upper surface of the lamina. Lower surface: Lower surface venation is colored the same as the lower surface of the lamina.

Inflorescence description:

*Arrangement*.—Terminal panicle.

*Position*.—Upright and above the foliage.

*Type and form*.—Panicle, consisting of a main panicle and an average of 12 secondary panicles, each consisting of an average of 9 individual flowers.

*Height*.—Average 12.6 cm, excluding peduncle.

*Diameter*.—Average 10.7 cm.

*Quantity of inflorescence per plant*.—1.

*Quantity of flowers per inflorescence*.—Average 25.

*Quantity of flowers and flower buds per plant*.—Average 85.

*Natural flowering season*.—Continuously.

*Time to flower or response time*.—6 months.

*Flower bud*.—Length: Average 1.4 cm. Diameter: Average 0.6 cm. Shape: Ovate. Texture: Smooth and glabrous. Luster: Slightly glossy. Color: 12B (yellow) and tipped 157D (green-white).

*Flower*.—Type and form: Single, rotate. Aspect: Outwardly to upright. Habit: Freely flowering. Fragrance: Not fragrant. Shape: Rotate, petals not opening but remaining in oblanceolate shape. Vertical height: Average 0.8 cm. Horizontal diameter: Average 0.8 cm. Length (depth): Average 2.4 cm. Texture (both sides): Smooth and glabrous. Longevity: Average 4 weeks. Persistence: Persistent.

*Petals*.—Arrangement: Rotate. Quantity per flower: Average 3. Number of petal whorls: Average 1. Petal fusion: Not fused. Length: Average 1.6 cm. Width: Average 0.5 cm. Shape: Oblong, slightly concave. Apex: Bluntly acute. Base: Cuneate. Margin: Entire. Margin undulation: Non undulating. Texture (both upper and lower surfaces): Smooth and glabrous. Rugosity (both upper and lower surfaces): Nonrugose. Luster (both upper and lower surfaces): Moderately glossy. Color, when opening: Upper surface: 8C and 8D (yellow) and transitioning 155C (white) towards and at the apex. Lower surface: 9C (yellow) and transitioning 155C (white) towards and at the apex. Color when fully opened: Upper surface: 8C and 8D (yellow) and transitioning 155C (white) towards and at the apex. Lower surface: 9C (yellow) and transitioning 155C (white) towards and at the apex. Color when fading (both upper and lower surfaces): 200B (brown). Venation: Inconspicuous. Petaloids: Not present.

*Calyx*.—Shape: Rotate. Length: Average 1.7 cm. Diameter: Average 0.8 cm.

*Sepals*.—Arrangement: Rotate. Quantity per flower: Average 3. Quantity of sepal whorls: Average 1. Length: Average 1.3 cm. Width: Average 0.6 cm. Sepal fusion: Not fused. Shape: Ovate, concave. Apex or tip: Acute. Base: Cuneate. Margin: Entire. Texture (both upper and lower surfaces): Smooth and glabrous. Luster: Upper surface: Slightly glossy. Lower surface: Moderately glossy. Color when opening: Upper surface: 22A and 22B (yellow-orange). Lower surface: 22B (yellow-orange) and tinged 31B (orange-red) towards the apex. Color when fully opened: Upper surface: 31D (orange-red). Lower surface: 22C and 22D (yellow-orange) and strongly tinged 34C (orange-red). Sepal spurs: Not present.

*Peduncle*.—Length: Average 37.5 cm Diameter: Average 1.1 cm. Orientation: Vertical. Strength: Strong. Texture: Smooth and glabrous; lower part below the panicle is moderately covered in a felt, slightly rough to the touch and colored 156D (greyed- white). Luster: Matte. Color: 46A (red) and blushed 199C and 199D (greyed-yellow and grey- brown); secondary peduncles colored 46A (red).

*Pedicels*.—Not present.

*Scape bracts*.—General description: An average of 10 scape bracts present at the base of the inflorescence and on the scape (peduncle). Shape: Broad ovate and strongly concave. Length: Average 4.8 cm. Width: Average 3.7 cm. Luster: Upper surface: Matte. Lower surface: Very slightly glossy. Margins: Finely serrate. Apex: Apiculate with a pungent tip. Base: Broad cuneate. Color (both upper and lower surfaces): 44A (red); the upper surface of the lower scape bracts banded with 197D (greyed-green) near the top; the lower surface of the lower scape bracts banded with 148A (yellow-green) near the top.

*Primary bracts*.—General description: At the base of each secondary panicle, a single fertile bract is present. Shape: Ovate and concave. Length: Average 1.6 cm. Width: Average 0.8 cm. Luster (both upper and lower surfaces): Matte. Margin: Entire. Apex: Apiculate. Base: Broad cuneate. Color (both upper and lower surfaces): 43A (red) and tipped 199C and 199D (grey-brown); lower surface moderately covered with a felt colored 156D (greyed-white).

*Floral bracts*.—General description: Below each individual flower, a single floral bract is present. Shape: Broad ovate. Length: Average 1.0 cm. Width: Average 0.8 cm. Margin: Entire. Apex: Apiculate. Base: Cuneate. Color (both upper and lower surfaces): 50B and 50C (red).

Reproductive organs:

*Stamens*.—Quantity per flower: Average 3. Length: Average 1.5 cm.

*Filament*.—Length: Average 1.2 cm. Color: 2D (yellow).

*Anther*.—Shape: Dorsifixed, narrow elliptic. Length: Average 0.3 cm. Width: Average 0.1 cm. Color: 16B (yellow-orange). Pollen amount: Low. Pollen color: 16C (yellow-orange).

*Pistil*.—Quantity per flower: 1. Length: Average 0.5 cm.

*Stigma*.—Shape: Cleft shaped, three parted and fringed. Length: Average 0.1 cm. Diameter: Average 0.1 cm. Color: NN155A (white).

*Style*.—Length: Average 0.4 cm. Color: 15C (yellow-orange).

*Ovary color*.—11A (yellow-orange).

Fruit and seed set: None observed to date.

Temperature tolerances: USDA Zones 10 to 13; at least tolerant of temperatures to 40 degrees Celsius.

Rain tolerance: High.

Wind tolerance: High.

Disease and pest tolerance: No claims are made to any superior disease or insect resistance or tolerance.

COMPARISON WITH THE PARENT PLANTS

The new *Aechmea* cultivar 'A2191' can be distinguished from its female or seed parent in the following characteristics described in Table 1 below.

TABLE 1

| Characteristic | 'A2191' | Female parent |
|---|---|---|
| Overall plant habit | Compact and upright rosette | Medium and open rosette |
| Leaf surface pattern | Strong and uniform silver banding | Weak silver banding |
| Leaf color (upper surface) | Dark green with silver bands | Green, slightly dull |
| Inflorescence position | Upright and above foliage | Partly within rosette |
| Inflorescence color | Deep red | Orange-red |
| Floral bract width | Broad | Narrow |
| Overall appearance | Compact and uniform | Moderately vigorous |

The new *Aechmea* cultivar 'A2191' can be distinguished from its male or pollen parent in the following characteristics described in Table 2 below.

TABLE 2

| Characteristic | 'A2191' | Male Parent |
|---|---|---|
| Overall plant habit | Compact and upright rosette | More spreading rosette |
| Leaf banding | Strong and uniform silver banding | Irregular and weak |
| Leaf color (upper surface) | Dark green with silver overlay | Light green |

TABLE 2-continued

| Characteristic | 'A2191' | Male Parent |
|---|---|---|
| Inflorescence position | Upright and above foliage | Medium |
| Inflorescence color | Deep red | Orange-red |
| Flower density | High | Moderate |
| Plant vigor | Strong and uniform | Moderate |

COMPARISON WITH RELATED KNOWN VARIETY

The new *Aechmea* cultivar 'A2191' can be distinguished from the related known variety of *Aechmea* 'Pepita' in the following characteristics described in Table 3 below.

TABLE 3

| Characteristic | 'A2191' | 'Pepita' |
|---|---|---|
| Overall plant habit | Compact and upright rosette | Larger, more spreading rosette |
| Leaf banding | Strong and uniform silver banding | Absent or weak |
| Leaf color (upper surface) | Dark greenwith silver overlay | Green |
| Inflorescence size | Compact and proportionate | Medium |
| Inflorescence color | Deep red | Orange-red |
| Scape bract color | Deep red | Light-red |
| Overall appearance | Highly uniform and ornamental | Moderate uniformity |

What is claimed is:

1. A new and distinct cultivar of *Aechmea* plant named 'A2191', substantially as illustrated and described herein.

* * * * *